United States Patent [19]
Oxman et al.

[11] Patent Number: 5,980,253
[45] Date of Patent: Nov. 9, 1999

[54] PROCESS FOR TREATING HARD TISSUES

[75] Inventors: Joel D. Oxman, St. Louis Park; Hoa T. Bui, Mendota Heights, both of Minn.; Dwight W. Jacobs, Hudson, Wis.

[73] Assignee: 3M Innovative Properties Company, St. Paul, Minn.

[21] Appl. No.: 09/005,885

[22] Filed: Jan. 12, 1998

[51] Int. Cl.$^6$ .............. A61B 17/06; A61K 6/08; A61C 5/00; C08L 63/00
[52] U.S. Cl. ............ 433/228.1; 522/25; 522/28; 522/29; 522/31; 522/81; 522/83; 522/66; 522/170; 522/182; 522/908; 523/116; 206/63.5; 106/35
[58] Field of Search ................. 522/170, 25, 29, 522/28, 182, 31, 81, 83, 908; 523/116; 433/228.1; 206/63.5; 106/35

[56] References Cited

U.S. PATENT DOCUMENTS

| | | | |
|---|---|---|---|
| 4,228,062 | 10/1980 | Lee, Jr. et al. | 260/42.28 |
| 4,694,029 | 9/1987 | Land | 522/8 |
| 4,719,149 | 1/1988 | Aasen et al. | 428/473 |
| 4,771,112 | 9/1988 | Engelbrecht | 525/327.3 |
| 5,512,611 | 4/1996 | Mitra | 523/116 |
| 5,545,676 | 8/1996 | Palazzotto et al. | 522/15 |
| 5,808,108 | 9/1998 | Chappelow et al. | 523/116 |
| 5,814,682 | 9/1998 | Rusin et al. | 523/116 |

FOREIGN PATENT DOCUMENTS

| | | |
|---|---|---|
| 0 330 117 | 8/1989 | European Pat. Off. |
| 0 678 533 A2 | 10/1995 | European Pat. Off. |
| 0 361 542 A1 | 8/1996 | European Pat. Off. |
| 0 728 790 A1 | 8/1996 | European Pat. Off. |
| 0728790 | 8/1996 | European Pat. Off. |
| 196 08 313 | 8/1997 | Germany |
| 1-174523 | 7/1989 | Japan |
| 688193 | 9/1979 | Russian Federation |
| 782200 | 9/1981 | Russian Federation |
| 2057522 | 4/1996 | Russian Federation |
| WO 96/13538 | 5/1996 | WIPO |

*Primary Examiner*—Susan W. Berman

[57] ABSTRACT

In a first aspect, a method for treating hard tissue that includes: (a) applying to hard tissue a composition that includes a cationically active functional group, a free radically active functional group, and a polymerization initiator capable of initiating free radical polymerization, where the number of moles of cationically active functional groups per gram of composition is no greater than about 0.0075; and (b) exposing the composition to polymerization conditions to form an adhesive bonded to the hard tissue.

In a second aspect, a method for treating hard tissue that includes: (a) applying to hard tissue a first polymerizable composition that includes a free radically active functional group and a polymerization initiator capable of initiating free radical polymerization, but is essentially free of polymerizable components having cationically active functional groups and is capable of forming an adhesive bonded to the hard tissue upon exposure to polymerization conditions; (b) applying a second polymerizable composition; and (c) exposing the second composition to polymerization conditions to form a hardened composition adhered to the hard tissue. The second composition includes (i) a cationically active functional group and (ii) an polymerization initiator capable of initiating cationic polymerization.

54 Claims, No Drawings

PROCESS FOR TREATING HARD TISSUES

BACKGROUND OF THE INVENTION

This invention relates to treating hard tissues such as tooth enamel or dentin.

Dental compositions such as composites, sealants, and cements generally will not bond sufficiently to tooth enamel or dentin unless the enamel or dentin is pre-treated with an adhesive layer. Typically, the enamel is etched with an acidic solution, followed by application of an unfilled methacrylate-based pre-adhesive composition that is polymerized using a thermally or photochemically activated free radical initiator system to form a layer of adhesive. The dental composition, which is typically a filled methacrylate-based composition, is then placed over the adhesive and polymerized using a free radical initiator system to form a hard, wear-resistant material. The adhesive, therefore, bonds to both the acid-etched tooth and to the dental composition.

Methacrylate-based dental compositions exhibit a relatively high degree of volumetric shrinkage upon polymerization. Accordingly, cationically curable compositions, and hybrid compositions featuring both cationically and free radically curable components, have been suggested as alternatives. Such compositions, which typically include epoxy resins as the cationically curable component, exhibit less shrinkage upon cure than the methacrylate-based compositions.

SUMMARY OF THE INVENTION

The inventors have discovered that pre-adhesive compositions containing relatively large amounts of cationically curable groups do not bond well to hard tissues such as tooth enamel and dentin. It is believed that the tooth inhibits polymerization of such materials. On the other hand, in the case of cationically curable dental compositions, conventional wisdom would dictate that it is desirable for the adhesive to contain a substantial number of cationically curable groups as well.

The inventors have discovered two ways of attacking this problem. One approach is to prepare a hybrid pre-adhesive composition that includes free radically active functional groups and a limited amount of cationically active functional groups. The inventors have discovered that such compositions successfully polymerize on the surface of hard tissue to form a strong bond with the hard tissue, yet at the same time can successfully bond to compositions that include cationically active groups.

The second approach is to eliminate cationically active groups altogether from the pre-adhesive composition, but engineer the pre-adhesive composition so that it still bonds to a subsequently applied composition that includes cationically active groups. Preferably, this is accomplished by incorporating functional groups such as hydroxyl groups in the pre-adhesive composition that can covalently bond to the subsequently applied composition.

In both approaches, the compositions are preferably free of components in amounts that would detrimentally affect polymerization of the cationically active functional groups of the pre-adhesive composition, polymerization of a subsequently applied cationically polymerizable composition, or both.

Accordingly, in a first aspect, the invention features a method for treating hard tissue that includes: (a) applying to hard tissue a composition that includes a cationically active functional group, a free radically active functional group, and a polymerization initiator capable of initiating free radical polymerization, where the number of moles of cationically active functional groups per gram of composition is no greater than about 0.0075; and (b) exposing the composition to polymerization conditions to form an adhesive bonded to the hard tissue. Preferably, the number of moles of cationically active functional groups is no greater than about 0.002. Prior to treatment with the composition, the hard tissue may be treated with an agent selected from the group consisting of etchants, primers, adhesion promoters, and combinations thereof.

As used herein, a "cationically active functional group" refers to a chemical moiety that is activated in the presence of an initiator capable of initiating cationic polymerization such that it is available for reaction with other compounds bearing cationically active functional groups. A "free radically active functional group" refers to a chemical moiety that is activated in the presence of an initiator capable of initiating free radical polymerization such that it is available for reaction with other compounds bearing free radically active functional groups.

The composition is preferably exposed to visible light in order to form the adhesive bonded to the hard tissue; the composition may also be auto-cured. The strength of the bond formed between the adhesive and the hard tissue preferably is at least about 3 MPa. The method is particularly useful where the hard tissue is a tooth (e.g., tooth enamel or dentin).

Suitable components of the composition include epoxy resins (which contain cationically active epoxy groups) and ethylenically unsaturated compounds (which contain free radically active unsaturated groups), preferably in combination with each other. Examples of useful ethylenically unsaturated compounds include acrylic acid esters, methacrylic acid esters, and combinations thereof. Also suitable are polymerizable components that contain both a cationically active group and a free radically active group in a single molecule. Examples include epoxy-functional acrylic acid esters, methacrylic acid esters, and combinations thereof.

The composition may also include a hydroxy-functional component. The hydroxy functional group may be present in combination with an ethylenically unsaturated group, e.g., in the form of a hydroxy-functional acrylic acid ester, a hydroxy-functional methacrylic acid ester, or combination thereof, or in combination with a cationically active functional group such as an epoxy. It may also be present in the form of a separate molecule, e.g., a polyol such as a polyether polyol.

Suitable polymerization initiators include initiators that initiate polymerization of free radically active functional groups. Such initiators may additionally initiate polymerization of cationically active functional groups.

One example of a suitable polymerization initiator includes an iodonium salt, preferably in combination with a visible light sensitizer. Particularly preferred are initiators that include an iodonium salt, a visible light sensitizer, and an electron donor in which the initiator has a photoinduced potential greater than or equal to that of 3-dimethylamino benzoic acid in a standard solution of $2.9 \times 10^{-5}$ moles/g diphenyl iodonium hexafluoroantimonate and $1.5 \times 10^{-5}$ moles/g camphorquinone in 2-butanone. Also suitable are auto-cure initiators that rely upon a chemical reaction, e.g., between a peroxide and an amine to trigger the polymerization process.

The method may further include applying a dental material (e.g., a dental composite such as a dental restorative) to either the adhesive or to the composition prior to polymerization. In the latter case, polymerization to form the adhesive takes place subsequent to application of the dental material. For example, polymerization to form the adhesive may take place concurrently with polymerization of the dental material. An example of a useful dental material is a dental composite that includes a cationically active functional group, a polymerization initiator (e.g., an iodonium salt), and a filler; the composite may further include a free radically active functional group.

The invention further features a kit that includes the above-described composition and a dental material capable of bonding to the adhesive. The dental material may be a dental composite such as a dental restorative. Preferably, the dental composite includes a cationically active functional group, a polymerization initiator, and a filler. The dental composite may include a free radically active functional group as well.

The invention also features a hard tissue sample such as a tooth having a surface treated with the above-described bonding composition.

In a second aspect, the invention features a method for treating hard tissue that includes: (a) applying to hard tissue a first polymerizable composition that includes a free radically active functional group and a polymerization initiator capable of initiating free radical polymerization, but is essentially free of polymerizable components having cationically active functional groups; (b) applying a second polymerizable composition; and (c) polymerizing the second composition to form a hardened composition adhered to the hard tissue. The second composition includes (i) a cationically active functional group and (ii) an polymerization initiator capable of initiating cationic polymerization.

The first composition is capable of forming an adhesive bonded to the hard tissue upon exposure to polymerization conditions. Polymerization to form the adhesive may take place prior to application of the second composition, or subsequent to application of the second composition. For example, in the latter case polymerization to form the adhesive may take place concurrently with polymerization of the second composition. Prior to treatment with the first polymerizable composition, the hard tissue may be treated with an agent selected from the group consisting of etchants, primers, adhesion promoters, and combinations thereof.

The method is particularly useful where the hard tissue is a tooth (e.g., tooth enamel or dentin). In such cases, the second composition preferably is a dental material, e.g., a dental composite such as a dental restorative.

The first composition preferably includes a functional group capable of covalently bonding to the second composition. An example of such a functional group is a hydroxyl group. The functional group may be present in the form of a separate molecule (e.g., a polyol). It may also be present in the form of a molecule that includes a free radically active or cationically active functional group as well. Examples of the former include hydroxy-functional acrylic acid esters, hydroxy-functional methacrylic acid esters, and combinations thereof, whereas examples of the latter include hydroxy-functional epoxy resins.

The second composition preferably includes an epoxy resin (which contains cationically active groups). It may also include a free radically active functional group, e.g., in the form of an acrylic acid ester, a methacrylic acid ester, or a combination thereof. The second composition may also include a component that includes both a cationically active functional group and a free radically active functional group in a single molecule. Examples of such components include epoxy-functional acrylic acid esters, epoxy-functional methacrylic acid esters, and combinations thereof.

At least one of the initiators may include an iodonium salt, preferably in combination with a visible light sensitizer. Particularly preferred are initiators that include an iodonium salt, a visible light sensitizer, and an electron donor in which the initiator has a photoinduced potential greater than or equal to that of 3-dimethylamino benzoic acid in a standard solution of $2.9 \times 10^{-5}$ moles/g diphenyl iodonium hexafluoroantimonate and $1.5 \times 10^{-5}$ moles/g camphorquinone in 2-butanone.

The invention further features a kit that includes the above-described first and second polymerizable compositions according to the second aspect of the invention, as well as a hard tissue sample such as a tooth having a surface treated with these two compositions.

The invention provides adhesives prepared from compositions having limited numbers of cationically active groups, or no cationically active groups, that adhere well to hard tissue such as tooth enamel and dentin. Such adhesives also adhere well to both cationically polymerizable and free radically polymerizable compositions, particularly where the adhesive contains functional groups such as hydroxyl groups that are capable of covalently bonding to the cationically polymerizable or free radically polymerizable composition. The adhesives are useful in a variety of applications, including bonding dental compositions such as dental composites to tooth enamel or dentin, particularly where the dental composition includes a cationically polymerizable component such as an epoxy resin.

Other features and advantages of the invention will be apparent from the following description of the preferred embodiments thereof, and from the claims.

DETAILED DESCRIPTION

Adhesive Bonding Compositions

Adhesive bonding compositions are prepared from pre-adhesive compositions having a free radically active functional group and either limited amounts of cationically active functional groups, or no cationically active functional groups. Preferably, the number of moles of cationically active functional groups per gram of pre-adhesive composition is no greater than about 0.0075, more preferably no greater than about 0.002. The pre-adhesive composition also preferably contains functional groups such as hydroxyl groups capable of covalently bonding to a subsequently applied composition such as a dental composite, sealant, or cement. In addition, the pre-adhesive compositions are preferably free of components in amounts that would detrimentally affect polymerization of the cationically active functional groups of the pre-adhesive composition, polymerization of a subsequently applied cationically polymerizable composition, or both.

Materials having free radically active functional groups include monomers, oligomers, and polymers having one or more ethylenically unsaturated groups. Suitable materials contain at least one ethylenically unsaturated bond, and are capable of undergoing addition polymerization. Such free radically polymerizable materials include mono-, di- or poly- acrylates and methacrylates such as methyl acrylate, methyl methacrylate, ethyl acrylate, isopropyl methacrylate, n-hexyl acrylate, stearyl acrylate, allyl acrylate, glycerol diacrylate, glycerol triacrylate, ethyleneglycol diacrylate, diethyleneglycol diacrylate, triethyleneglycol dimethacrylate, 1,3-propanediol diacrylate, 1,3-propanediol dimethacrylate, trimethylolpropane triacrylate, 1,2,4-butanetriol trimethacrylate, 1,4-cyclohexanediol diacrylate, pentaerythritol triacrylate, pentaerythritol tetraacrylate, pentaerythritol tetramethacrylate, sorbitol hexacrylate, bis[1-(2-acryloxy)]-p-ethoxyphenyldimethylmethane, bis[1-(3-acryloxy-2-hydroxy)]-p-propoxyphenyldimethylmethane, and trishydroxyethyl-isocyanurate trimethacrylate; the bis-acrylates and bis-methacrylates of polyethylene glycols of molecular weight 200–500, copolymerizable mixtures of acrylated monomers such as those in U.S. Pat. No. 4,652,274, and acrylated oligomers such as those of U.S. Pat. No. 4,642,126; and vinyl compounds such as styrene, diallyl phthalate, divinyl succinate, divinyl adipate and divinylphthalate. Mixtures of two or more of these free radically polymerizable materials can be used if desired.

Materials having cationically active functional groups include cationically polymerizable epoxy resins. Such materials are organic compounds having an oxirane ring, i.e., a group of the formula

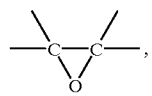

which is polymerizable by ring opening. These materials include monomeric epoxy compounds and epoxides of the polymeric type and can be aliphatic, cycloaliphatic, aromatic or heterocyclic. These materials generally have, on the average, at least 1 polymerizable epoxy group per molecule, preferably at least about 1.5 and more preferably at least about 2 polymerizable epoxy groups per molecule. The polymeric epoxides include linear polymers having terminal epoxy groups (e.g., a diglycidyl ether of a polyoxyalkylene glycol), polymers having skeletal oxirane units (e.g., polybutadiene polyepoxide), and polymers having pendent epoxy groups (e.g., a glycidyl methacrylate polymer or copolymer). The epoxides may be pure compounds or may be mixtures of compounds containing one, two, or more epoxy groups per molecule. The Aaverage™ number of epoxy groups per molecule is determined by dividing the total number of epoxy groups in the epoxy-containing material by the total number of epoxy-containing molecules present.

These epoxy-containing materials may vary from low molecular weight monomeric materials to high molecular weight polymers and may vary greatly in the nature of their backbone and substituent groups. For example, the backbone may be of any type and substituent groups thereon can be any group that does not substantially interfere with cationic polymerization at room temperature. Illustrative of permissible substituent groups include halogens, ester groups, ethers, sulfonate groups, siloxane groups, nitro groups, phosphate groups, and the like. The molecular weight of the epoxy-containing materials may vary from about 58 to about 100,000 or more.

Useful epoxy-containing materials include those which contain cyclohexene oxide groups such as epoxycyclohexanecarboxylates, typified by 3,4-epoxycyclohexylmethyl-3,4-epoxycyclohexanecarboxylate, 3,4-epoxy-2-methylcyclohexylmethyl-3,4-epoxy-2-methylcyclohexane carboxylate, and bis(3,4-epoxy-6-methylcyclohexylmethyl) adipate. For a more detailed list of useful epoxides of this nature, reference is made to the U.S. Pat. No. 3,117,099, which is incorporated herein by reference.

Further epoxy-containing materials which are useful in the compositions of this invention include glycidyl ether monomers of the formula

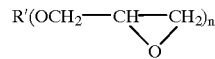

where R= is alkyl or aryl and n is an integer of 1 to 6. Examples are glycidyl ethers of polyhydric phenols obtained by reacting a polyhydric phenol with an excess of chlorohydrin such as epichlorohydrin (e.g., the diglycidyl ether of 2,2-bis-(2,3-epoxypropoxyphenol)-propane). Further examples of epoxides of this type are described in U.S. Pat. No. 3,018,262, which is incorporated herein by reference, and in Handbook of Epoxy Resins by Lee and Neville, McGraw-Hill Book Co., New York (1967).

There are a host of commercially available epoxy resins which can be used in this invention. In particular, epoxides which are readily available include octadecylene oxide, epichlorohydrin, styrene oxide, vinyl cyclohexene oxide, glycidol, glycidylmethacrylate, diglycidyl ether of Bisphenol A (e.g., those available under the trade designations Epon 828™, Epon 825™, Epon 1004™ and Epon 1010™ from Shell Chemical Co., DER-333™, DER-332™, and DER-334™, from Dow Chemical Co.), vinylcyclohexene dioxide (e.g., ERL-4206™ from Union Carbide Corp.), 3,4-epoxycyclohexylmethyl-3,4-epoxycyclohexene carboxylate (e.g., ERL-4221™ or CYRACURE UVR 6110™ or UVR 6105™ from Union Carbide Corp.), 3,4-epoxy-6-methylcyclohexylmethyl-3,4-epoxy-6-methyl-cyclohexene carboxylate (e.g., ERL-4201™ from Union Carbide Corp.), bis(3,4-epoxy-6-methylcyclohexylmethyl) adipate (e.g., ERL-4289™ from Union Carbide Corp.), bis(2,3-epoxycyclopentyl) ether (e.g., ERL-0400™ from Union Carbide Corp.), aliphatic epoxy modified from polypropylene glycol (e.g., ERL-4050™ and ERL-4052™ from Union Carbide Corp.), dipentene dioxide (e.g., ERL-4269™ from Union Carbide Corp.), epoxidized polybutadiene (e.g., Oxiron 2001™ from FMC Corp.), silicone resin containing epoxy functionality, flame retardant epoxy resins (e.g., DER-580™, a brominated bisphenol type epoxy resin available from Dow Chemical Co.), 1,4-butanediol diglycidyl ether of phenolformaldehyde novolak (e.g., DEN-431 ™ and DEN-438™ from Dow Chemical Co.), and resorcinol diglycidyl ether (e.g., Kopoxite™ from Koppers Company, Inc.), bis(3,4-epoxycyclohexyl)adipate (e.g., ERL-4299™ or TVR-6128™, from Union Carbide Corp.), 2-(3,4-epoxycyclohexyl-5, 5-spiro-3,4-epoxy) cyclohexane-meta-dioxane (e.g., ERL-4234™ from Union Carbide Corp.), vinylcyclohexene monoxide 1,2-epoxyhexadecane (e.g., UVR-6216™ from Union Carbide Corp.), alkyl glycidyl ethers such as alkyl $C_8$–$C_{10}$ glycidyl ether (e.g., HELOXY Modifier 7™ from Shell Chemical Co.), alkyl $C_{12}$–$C_{14}$ glycidyl ether (e.g., HELOXY Modifier 8™ from Shell Chemical Co.), butyl glycidyl ether (e.g., HELOXY Modifier 61™ from Shell Chemical Co.), cresyl glycidyl ether (e.g., HELOXY Modifier 62™ from Shell Chemical Co.), p-ter butylphenyl glycidyl ether (e.g., HELOXY Modifier 65™ from Shell Chemical Co.), polyfunctional glycidyl ethers such as diglycidyl ether of 1,4-butanediol (e.g., HELOXY Modifier 67™ from Shell Chemical Co.), diglycidyl ether of neopentyl glycol (e.g., HELOXY Modifier 68™ from Shell Chemical Co.), diglycidyl ether of cyclohexanedimethanol (e.g., HELOXY Modifier 107™ from Shell Chemical Co.), trimethylol ethane triglycidyl ether (e.g., HELOXY Modifier 44™ from Shell Chemical Co.), trimethylol propane triglycidyl ether (e.g., HELOXY Modifier 48™ from Shell Chemical Co.), polyglycidyl ether of an aliphatic polyol (e.g., HELOXY Modifier 84™ from Shell Chemical Co.), polyglycol diepoxide (e.g., HELOXY Modifier 32™ from Shell Chemical Co.), bisphenol F epoxides (e.g., EPN-1138™ or GY-281™ from Ciba-Geigy Corp.), 9,9-bis[4-(2,3-epoxypropoxy)-phenyl]fluorenone (e.g., Epon 1079™ from Shell Chemical Co.).

Still other epoxy resins contain copolymers of acrylic acid esters or glycidol such as glycidylacrylate and glycidylmethacrylate with one or more copolymerizable vinyl compounds. Examples of such copolymers are 1:1 styrene-glycidylmethacrylate, 1:1 methylmethacrylate-glycidylacrylate and a 62.5:24:13.5 methylmethacrylate-ethyl acrylate-glycidylmethacrylate.

Other useful epoxy resins are well known and contain such epoxides as epichlorohydrins, alkylene oxides, e.g., propylene oxide, styrene oxide; alkenyl oxides, e.g., butadiene oxide; glycidyl esters, e.g., ethyl glycidate.

The polymers of the epoxy resin can optionally contain other functionalities that do not substantially interfere with cationic polymerization at room temperature.

Blends of various epoxy-containing materials are also contemplated. Examples of such blends include two or more weight average molecular weight distributions of epoxy-containing compounds, such as low molecular weight (below 200), intermediate molecular weight (about 200 to 10,000) and higher molecular weight (above about 10,000). Alternatively or additionally, the epoxy resin may contain a blend of epoxy-containing materials having different chemical natures, such as aliphatic and aromatic, or functionalities, such as polar and non-polar.

Other types of useful materials having cationically active functional groups include vinyl ethers, oxetanes, spiro-orthocarbonates, spiro-orthoesters, and the like.

If desired, both cationically active and free radically active functional groups may be contained in a single molecule. Such molecules may be obtained, for example, by reacting a di- or poly-epoxide with one or more equivalents of an ethylenically unsaturated carboxylic acid. An example of such a material is the reaction product of UVR-6105 (available from Union Carbide) with one equivalent of methacrylic acid. Commercially available materials having epoxy and free-radically active functionalities include the Cyclomer™ series, such as Cyclomer M-100, M-101, or A-200 available from Daicel Chemical, Japan, and Ebecryl™-3605 available from Radcure Specialties.

Suitable hydroxyl-containing materials can be any organic material having hydroxyl functionality of at least 1, and preferably at least 2. Preferably, the hydroxyl-containing material contains two or more primary or secondary aliphatic hydroxyl groups (i.e., the hydroxyl group is bonded directly to a non-aromatic carbon atom). The hydroxyl groups can be terminally situated, or they can be pendent from a polymer or copolymer. The molecular weight of the hydroxyl-containing organic material can vary from very low (e.g., 32) to very high (e.g., one million or more). Suitable hydroxyl-containing materials can have low molecular weights, i.e. from about 32 to 200, intermediate molecular weight, i.e. from about 200 to 10,000, or high molecular weight, i.e. above about 10,000. As used herein, all molecular weights are weight average molecular weights. The hydroxyl-containing material can optionally contain other functionalities that do not substantially interfere with cationic polymerization at room temperature. Thus, the hydroxyl-containing materials can be non-aromatic in nature or can contain aromatic functionality. The hydroxyl-containing material can optionally contain heteroatoms in the backbone of the molecule, such as nitrogen, oxygen, sulfur, and the like, provided that the ultimate hydroxyl-containing material does not substantially interfere with cationic polymerization at room temperature. The hydroxyl-containing material can, for example, be selected from naturally occurring or synthetically prepared cellulosic materials. Of course, the hydroxyl-containing material is also substantially free of groups which may be thermally or photolytically unstable;

that is, the material will not decompose or liberate volatile components at temperatures below about 100° C. or in the presence of actinic light which may be encountered during the desired polymerization conditions for the free radically active components of the pre-adhesive composition.

Representative examples of suitable hydroxyl-containing materials having a hydroxyl functionality of 1 include alkanols, monoalkyl ethers of polyoxyalkyleneglycols, monoalkyl ethers of alkylene-glycols, and others known in the art.

Representative examples of useful monomeric polyhydroxy organic materials include alkylene glycols (e.g., 1,2-ethanediol; 1,3-propanediol; 1,4-butanediol; 1,6-hexanediol; 1,8-octanediol; 2-ethyl-1,6-hexanediol; bis (hydroxymethyl)cyclohexane; 1,18-dihydroxyoctadecane; 3-chloro-1,2-propanediol); polyhydroxyalkanes (e.g., glycerine, tri-methylolethane, pentaerythritol, sorbitol) and other polyhydroxy compounds; 2-butyne-1,4-diol; 4,4-bis (hydroxymethyl)diphenylsulfone; castor oil; and the like.

Representative examples of useful polymeric hydroxyl-containing materials include polyoxyethylene and polyoxypropylene glycols, and particularly the polyoxyethylene and polyoxypropylene glycol diols and triols having molecular weights from about 200 to about 10,000 corresponding to a hydroxy equivalent weight of 100 to 5000 for the diols or 70 to 3300 for triols; polytetramethylene ether glycols such as polytetrahydrofuran or "poly THF" of varying molecular weight; copolymers of hydroxypropyl and hydroxyethyl acrylates and methacrylates with other free radical-polymerizable monomers such as acrylate esters, vinyl halides, or styrene; copolymers containing pendent hydroxy groups formed by hydrolysis or partial hydrolysis of vinyl acetate copolymers, polyvinylacetal resins containing pendent hydroxyl groups; modified cellulose polymers such as hydroxyethylated and hydroxypropylated cellulose; hydroxy-terminated polyesters; hydroxy-terminated polylactones, and particularly the polycaprolactones; fluorinated polyoxyethylene or polyoxypropylene glycols; and hydroxy-terminated polyalkadienes.

Useful commercially available hydroxyl-containing materials include the "TERATHANE" series of polytetramethylene ether glycols such as "TERATHANE" 650, 1000, 2000 and 2900 (available from du Pont de Nemours, Wilmington, Del.) the "PEP" series of polyoxyalkylene tetrols having secondary hydroxyl groups such as "PEP" 450, 550 and 650; "BUTVAR" series of polyvinylacetal resins such as "BUTVAR" B-72A, B-73, B-76, B-90 and B-98 (available from Monsanto Chemical Company, St. Louis, Mo.); and the "FORMVAR" series of resins such as 7/70, 12/85, 7/95 S, 7/95E, 15/95S and 15/95E (available from Monsanto Chemical Company); the "TONE" series of polycaprolactone polyols such as "TONE" 0200, 0210, 0230,0240, 0300 and 0301 (available from Union Carbide); "PARAPLEX U-148" aliphatic polyester diol (available from Rohm and Haas, Philadelphia, Pa.), the "MULTRON" R series of saturated polyester polyols such as "MULTRON" R-2, R-12A, R-16, R-18, R-38, R-68 and R-74 (available from Mobay Chemical Co.); "KLUCEL E" hydroxypropylated cellulose having an equivalent weight of approximately 100 (available from Hercules Inc.); "Alcohol Soluble Butyrate" cellulose acetate butyrate ester having a hydroxyl equivalent weight of approximately 400 (available from Eastman Kodak Co., Rochester, N.Y.); polyether polyols such as polypropylene glycol diol (e.g., "ARCOL PPG-425", "Arcol PPG-725", "ARCOL PPG-1025", "ARCOL PPG-2025", ARCOL PPG-3025", "ARCOL PPG-4025" from ARCO Chemical Co.); polypropylene glycol triol (e.g., "ARCOL LT-28", "ARCOL LHT-42", "ARCOL LHT 112", "ARCOL LHT 240", "ARCOL LG-56", "ARCOL LG-168", "ARCOL LG-650" from ARCO Chemical Co.); ethylene oxide capped polyoxypropylene triol or diol (e.g., "ARCOL 11-27", "ARCOL 11-34", "ARCOL E-351", "ARCOL E-452", "ARCOL E-785", "ARCOL E-786" from ARCO Chemical Co.); ethoxylated bis-phenol A; propylene oxide or ethylene oxide-based polyols (e.g., "VORANOL" polyether polyols from the Dow Chemical Co.).

The amount of hydroxyl-containing organic material used in the compositions of the invention may vary over broad ranges, depending upon factors such as the compatibility of the hydroxyl-containing material with the epoxide and/or free radically polymerizable component, the equivalent weight and functionality of the hydroxyl-containing material, the physical properties desired in the final adhesive composition, the desired speed of photopolymerization, and the like.

Blends of various hydroxyl-containing materials are particularly contemplated in this invention. Examples of such blends include two or more molecular weight distributions of hydroxyl-containing compounds, such as low molecular weight (below 200), intermediate molecular weight (about 200 to 10,000) and higher molecular weight (above about 10,000). Alternatively, or additionally, the hydroxyl-containing material can contain a blend of hydroxyl-containing materials having different chemical natures, such as aliphatic and aromatic, or functionalities, such as polar and non-polar. As an additional example, one may use mixtures of two or more poly-functional hydroxy materials or one or more mono-functional hydroxy materials with poly-functional hydroxy materials.

The polymerizable material(s) can also contain hydroxyl groups and free radically active functional groups in a single molecule. Examples of such materials include hydroxyalkylacrylates and hydroxyalkylmethacrylates such as hydroxyethylacrylate, hydroxyethylmethacrylate; glycerol mono- or di-(meth)acrylate; trimethylolpropane mono- or di-(meth)acrylate, pentaerythritol mono-, di-, and tri-(meth)acrylate, sorbitol mono-, di-, tri-, tetra-, or penta-(meth)acrylate; and 2,2-bis[4-(2-hydroxy-3-methacryloxypropoxy)phenyl]propane.

The polymerizable material(s) can also contain hydroxyl groups and cationically active functional groups in a single molecule. An example is a single molecule that includes both hydroxyl groups and epoxy groups.

The pre-adhesive composition further includes one or more polymerization initiators. The initiator may initiate only free radical polymerization, or it may be capable of initiating both free radical and cationic polymerization. In the case of pre-adhesive compositions having both free radically active functional groups and cationically active functional groups, and designed for bonding cationically polymerizable compositions such as epoxy-containing dental composites, it is possible to include only a polymerization initiator capable of initiating free radical polymerization in the pre-adhesive composition. The cationically active groups of the pre-adhesive composition can then be polymerized simultaneously with the subsequently applied cationically polymerizable composition using the initiator capable of initiating cationic polymerization that is included in the latter composition.

One class of initiators capable of initiating polymerization of free radically active functional groups includes conventional chemical initiator systems such as a combination of a peroxide and an amine. These initiators, which rely upon a thermal redox reaction, are often referred to as "auto-cure catalysts."

A second class of initiators capable of initiating polymerization of free radically active functional groups includes photoinitiators, optionally combined with a photosensitizer or accelerator. Such initiators typically are capable of generating free radicals for addition polymerization at some wavelength between 200 and 800 nm. Examples include alpha-diketones, monoketals of alpha-diketones or ketoaldehydes, acyloins and their corresponding ethers, chromophore-substituted halomethyl-s-triazines, chromophore-substituted halomethyl-oxadiazoles, and aryliodonium salts.

Palazzotto et al., U.S. Pat. No. 5,545,676, which is incorporated herein by reference, describes ternary photoinitiation systems suitable for free radical polymerization. These systems include an iodonium salt, e.g., a diaryliodonium salt; a sensitizer capable of light absorption within the range of wavelengths between about 300 an about 1000 nanometers (with visible light sensitizers such as camphorquinone being preferred); and an electron donor having an oxidation potential that is greater than zero and less than or equal to that of p-dimethyoxybenzene (1.32 volts vs. S.C.E.).

Photoinitiator systems capable of initiating both free radical and cationic polymerization are described in Oxman et al., U.S. Ser. No. 08/838,835 filed Apr. 11, 1997 entitled "Ternary Photoinitiator System for Curing of Epoxy/Polyol Resin Compositions" and Oxman et al., U.S. Ser. No. 08/840,093 filed Apr. 11, 1997 entitled "Ternary Photoinitiator System for Curing of Epoxy Resins", both of which are assigned to the same assignee as the present application and incorporated herein by reference. These photoinitiator systems include an iodonium salt (e.g., an aryliodonium salt); a visible light sensitizer (e.g., camphorquinone), and an electron donor. The systems have a photoinduced potential greater than or equal to that of 3-dimethylaminobenzoic acid in a standard solution of $2.9 \times 10^{-5}$ moles/g diphenyl iodonium hexafluoroantimonate and $1.5 \times 10^{-5}$ moles/g camphorquinone in 2-butanone. The photoinduced potential can be evaluated in the following manner. A standard solution is prepared that contains $2.9 \times 10^{-5}$ moles/g of diphenyl iodonium hexafluoroantimonate and $1.5 \times 10^{-5}$ moles/g of camphorquinone in 2-butanone. A pH electrode is then immersed in the solution and a pH meter is calibrated to zero mV. A test solution of the standard solution and the compound is prepared next using the compound at a concentration of $2.9 \times 10^{-5}$ moles/g. This test solution is irradiated using blue light having a wavelength of about 400 to 500 nm having an intensity of about 200 to 400 mW/cm$^2$ for about 5 to 10 seconds at a distance of about 1 mm. Millivolts relative to the standard solution are then determined by immersing the pH electrode in the test solution and obtaining a mV reading on the pH meter. Useful donors are those compounds that provide a reading of at least 100 mV relative to the standard solution, and preferably provide a gel time for the compositions that is at least about 30 to 40 percent shorter than for compositions that do not contain the donor. Higher mV readings are generally indicative of greater activity.

In some instances there may be some uncertainty regarding the outcome of the above procedure. This may be due to questions or uncertainty arising from the instrumentation employed, from the way the procedure was carried out, or other factors, or one may wish to verify the suitability of a particular compound. A second test may be performed to verify the result obtained by following the above procedure and resolve any such uncertainty.

The second method involves the evaluation of the photoinduced potential of an initiator system that includes the compound compared to a system that includes 3-dimethylamino benzoic acid. For this method, a standard solution of $2.9 \times 10^{-5}$ moles/g diphenyl iodonium hexafluoroantimonate, $1.5 \times 10^{-5}$ moles/g camphorquinone and $2.9 \times 10^{-5}$ moles/g of 3-dimethylaminobenzoic acid in 2-butanone is prepared. A pH electrode is then immersed in the solution and a pH meter is calibrated to zero mV. The standard solution is irradiated with blue light having a wavelength of between about 400–500 nm and an intensity of about 200 to 400 mW/cm$^2$ for about 5 to 10 seconds using a focused light source such as a dental curing light at a distance of about 1 mm. After light exposure, the potential of the solution is measured by immersing a pH electrode in the irradiated standard solution and reading the potential in mV using a pH meter. A test solution is then prepared using $2.9 \times 10^{-5}$ moles/g of diphenyl iodonium hexafluoroantimonate, $1.5 \times 10^{-5}$ moles/g of camphorquinone and $2.9 \times 10^{-5}$ moles/g of the compound in 2-butanone. The test solution is irradiated and the photoinduced potential measured using the same technique as described for the standard solution. If the test solution has a photoinduced potential that is the same as or greater than that of the 3-dimethylaminobenzoic acid containing standard solution, then the compound is a useful donor.

Also suitable are binary photoinitiation systems that include an sensitizer and an electron donor, or a sensitizer and an iodonium salt. The former initiate only free radical polymerization, while the latter initiate both free radical and cationic polymerization.

The pre-adhesive compositions can also contain suitable adjuvants such as fluoride sources, anti-microbial agents, accelerators, stabilizers, absorbers, pigments, dyes, viscosity modifiers, surface tension depressants and wetting aids, antioxidants, and other ingredients well known to those skilled in the art. The amounts and types of each ingredient should be adjusted to provide the desired physical and handling properties before and after polymerization. In addition, the adjuvants should not be present in amounts that would detrimentally affect polymerization of any cationically active functional groups of the pre-adhesive composition, polymerization of a subsequently applied cationically polymerizable composition, or both.

The pre-adhesive compositions are prepared by admixing, under "safe light" conditions, the various components of the compositions. Suitable inert solvents may be employed if desired when effecting the mixture. Examples of suitable solvents include acetone, dichloromethane, and acetonitrile.

Bonding Applications

The pre-adhesive composition is applied in the form of a relatively thin layer to a hard tissue surface. Examples of hard tissue surfaces include teeth (the component parts of which are enamel, dentin, and cementum), bone, fingernails, and hoofs. Preferred hard tissue surfaces include dentin and enamel. Prior to application of the pre-adhesive composition, the hard tissue surface may be pre-treated or primed to enhance adhesion to the hard tissue surface (e.g., using an acid etchant).

Following application to the hard tissue surface, the pre-adhesive composition is preferably polymerized to form an adhesive layer on the hard tissue surface. Preferably, polymerization is effected by exposing the pre-adhesive composition to a radiation source, preferably a visible light source. Suitable visible light sources include a Visilux™ dental curing light commercially available from 3M Company of St. Paul, Minn. Such lights have an intensity of about 200 mW/cm$^2$ at a wavelength of 400–500 nm. In the case of pre-adhesive compositions having both free radically active functional groups and cationically polymerizable active groups, exposure to the radiation source may effect polymerization of the free radically active groups alone, or both the free radically and cationically active groups, depending upon the choice of initiator.

In the case of thermal redox initiation systems (i.e., auto-cure catalysts), the components of the initiation system (e.g., peroxide and amine) are combined with each other, and then added to the remainder of the pre-adhesive composition. The resulting composition is then applied to hard tissue and allowed to polymerize. Light activation is not necessary.

Following polymerization to form the adhesive, a second composition is applied to the adhesive. The adhesives are particularly usefull for bonding dental compositions, especially where the dental composition contains cationically active functional groups such as epoxy groups or vinyl ether groups. The dental compositions may be filled or unfilled, and include dental materials such as direct esthetic restorative materials (e.g., anterior and posterior restoratives), prostheses, sealants, veneers, cavity liners, crown and bridge cements, artificial crowns, artificial teeth, dentures, and the like.

The term "composite" as used herein refers to a filled dental material. The term "restorative" as used herein refers to a composite which is polymerized after it is disposed adjacent to a tooth. The term "prosthesis" as used herein refers to a composite which is shaped and polymerized for its final use (e.g., as crown, bridge, veneer, inlay, onlay or the like) before it is disposed adjacent to a tooth. The term "sealant" as used herein refers to a lightly filled composite or to an unfilled dental material which is polymerized after it is disposed adjacent to a tooth. "Polymerizable" refers to curing or hardening the dental material, e.g., by free-radical, cationic, or mixed reaction mechanisms.

In the case of dental compositions containing cationically active functional groups, the dental composition is polymerized via a cationic mechanism following application to the bonding adhesive. Suitable polymerization initiators incorporated into the polymerizable dental compositions include the initiators described above in the case of the adhesive composition that are capable of initiating both free radical and cationic polymerization. Also suitable are cationic-only initiators. Examples include onium salts with complex metal halide anions (e.g., diaryliodonium salts) and mixed ligand arene cyclopentadienyl metal salts of complex metal halide anions. A commercially available example of the latter is IRGACURE 261 which is available from Ciba Geigy.

The invention will now be described further by way of the following examples. Unless otherwise indicated, all parts and percentages are by weight.

EXAMPLES

Sample Preparation and Testing

Adhesives and composites were prepared by mixing individual ingredients together. Various combinations of adhesives and composites were then tested for adhesion to bovine teeth according to the following protocol.

Five bovine teeth of similar age and appearance were partially embedded in circular acrylic discs. The exposed portion of each tooth was ground flat and parallel to the acrylic disc using Grade 120 silicon carbide paper-backed abrasive mounted on a lapidary wheel in order to expose the enamel. Further grinding and polishing of the teeth was carried out by mounting Grade 320 silicon carbide paper-backed abrasive and then grade 600 silicon carbide paper-backed abrasive on the lapidary wheel. During the grinding and polishing steps, the teeth were continuously rinsed with water.

The polished teeth were stored in distilled water, and used for testing within 2 hours after polishing. The polished teeth were removed from the water and dried using a stream of compressed air. Next, SCOTCH BOND™ MULTIPURPOSE ETCHANT (3M Co., St. Paul, Minn.) was applied to the enamel surface for 15 seconds, rinsed with water, and then air-dried. A layer of pre-adhesive was then applied with a brush to the etched surface and exposed for 30 seconds to a "Visilux-2" dental curing light (3M Co., St. Paul, Minn.) to form a thin adhesive layer (approximately 50–150 microns thick).

Previously prepared molds made from a 2 mm thick "Teflon" sheet with a 5 mm diameter hole through the sheet were clamped to each polished tooth so that the central axis of the hole in the mold was normal to the polished tooth surface. The hole in each mold was filled with a visible light-polymerizable dental composite and exposed for 60 seconds to radiation from a "Visilux-2" dental curing light. The teeth and molds were allowed to stand for about 5 minutes at room temperature, after which they were stored in distilled water at 37° C. for 24 hours. The molds were then carefully removed from the teeth, leaving a molded button of dental composite attached to each tooth.

The adhesive strength between the composite and the tooth was evaluated by mounting the acrylic disk in a holder clamped in the jaws of an Instron apparatus with the polished tooth surface oriented parallel to the direction of pull. A loop of orthodontic wire (0.44 mm diameter) was placed around the button adjacent to the polished tooth surface. The ends of the orthodontic wire were clamped in the pulling jaw of the Instron, thereby placing the bond in shear stress (where "bond" refers to both the bond between the adhesive and the composite, and the bond between the adhesive and the tooth). Stress was applied using a crosshead speed of 2 mm/min. until the bond failed.

Five samples of each adhesive/composite combination were tested. The reported adhesion value represents the average of five samples and reflects the point at which failure occurred at either the adhesive/tooth interface or the adhesive/composite interface, whichever occurred first.

Examples 1–8

Eight pre-adhesive compositions were prepared and subsequently polymerized to form adhesive compositions, as described above. The compositions contained the following ingredients:

Example 1

| | |
|---|---|
| Resin: | 50.0 parts of 6 moles ethoxylated Bisphenol A-dimethacrylate ("BisEMA6"), 50.0 parts triethyleneglycol dimethacrylate ("TEGDMA"). |
| Initiator: | 0.25 parts camphorquinone ("CPQ"), 0.25 parts ethyl-p-dimethylaminobenzoate ("EDMAB"), 0.50 parts diaryliodonium hexafluoroantimonate (Sarcat ™ CD1012, Sartomer, Inc.). |

Example 2

| | |
|---|---|
| Resin: | 50.0 parts Bisphenol A diglycidyl ether dimethacrylate ("BisGMA"), 50.0 parts TEGDMA. |
| Initiator: | 0.25 parts CPQ, 0.25 parts EDMAB, 0.50 parts CD1012. |

Example 3

| | |
|---|---|
| Resin: | 61.9 parts BisGMA, 37.1 parts 2-hydroxyethyl methacrylate ("HEMA"). |
| Initiator: | 0.25 parts CPQ, 0.50 parts EDMAB, 0.40 parts diphenyl iodonium hexafluorophosphate. |

Example 4

Single Bond ™ Adhesive (3M Co., St. Paul, MN)

Example 5

| | |
|---|---|
| Resin: | 20.55 parts caprolactone modified cycloaliphatic monoepoxy mono-methacrylate ("M-101" commercially available from Daicel Chemical, Japan), 57.53 parts BisGMA, 21.92 parts hexanedioldiacrylate ("HDDA"). |
| Initiator: | 0.25 parts CPQ, 0.25 parts EDMAB, 0.50 parts CD1012. |

Example 6

| | |
|---|---|
| Resin: | 18.75 parts M-101, 52.5 parts BisGMA, 20.0 parts HDDA, 8.75 parts HEMA. |
| Initiator: | 0.25 parts CPQ, 0.25 parts EDMAB, 0.50 parts CD1012. |

Example 7

| | |
|---|---|
| Resin: | 72.0 parts 3,4-epoxycyclohexylmethyl-3,4-epoxy-cyclohexane carboxylate ("UVR6105"), 18.0 parts polytetrahydrofuran (MW = 250) ("p(THF)"), 10.0 parts HEMA. |
| Initiator: | 0.25 parts CPQ, 0.25 parts EDMAB, 0.50 parts CD1012. |

Example 8

| | |
|---|---|
| Resin: | 80.0 parts UVR6105, 20.0 parts p(THF). |
| Initiator: | 0.25 parts CPQ, 0.25 parts EDMAB, 0.50 parts CD1012. |

Each adhesive composition was used to bond three different filled dental composites to enamel, as described above. Each composite contained 21.5% by weight resin plus inititator and 78.5% by weight filler. The composites contained the following ingredients (all amounts in weight percent):

Methacrylate Composite

| | |
|---|---|
| Resin: | 50.0 parts BisGMA, 50.0 parts TEGDMA. |
| Initiator: | 0.50 parts CPQ, 0.10 parts EDMAB, 1.25 parts CD1012. |
| Filler: | Quartz filler as described above in the case of the Epoxy/Methacrylate composite. |

Epoxy/Methacrylate Composite

| | |
|---|---|
| Resin: | 72.0 parts UVR6105, 18.0 parts p(THF), 10.0 parts M-101. |
| Initiator: | 0.50 parts CPQ, 0.10 parts EDMAB, 1.25 parts CD1012. |
| Filler: | Quartz filler prepared from a 90/10 blend of ball-milled ground quartz and Cab-O-Sil M-5 (Cabot Corp., Tuscola, IL). The average particle size of the filler was 2.25–3.15 microns. |

Epoxy Composite

| | |
|---|---|
| Resin: | 42.0 parts UVR6105, 42.0 parts trimethylolpropane triglycidyl ether ("HELOXY-48"), 16.0% p(THF). |
| Initiator: | 0.50 parts CPQ, 0.10 parts EDMAB, 1.25 parts CD1012. |
| Filler: | Quartz filler as described above in the case of the Epoxy/Methacrylate composite. |

A total of 24 adhesive/composite combinations were tested. The adhesion values, in MPa, are shown in Table I.

TABLE I

| | | Composite | | |
|---|---|---|---|---|
| Example | Adhesive Functionality | Methacrylate | Epoxy/Methacrylate | Epoxy |
| 1 | Methacrylate | 12 | 6 | 3 |
| 2 | Methacrylate/OH | 11 | 14 | 14 |
| 3 | Methacrylate/OH | 14 | 13 | 8 |
| 4 | Methacrylate/OH/Urethane | 15 | 2 | 0 |
| 5 | Methacrylate/OH/Epoxy | 11 | 14 | 14 |
| 6 | Methacrylate/OH/Epoxy | 11 | 15 | 14 |
| 7 | Epoxy/OH/Methacrylate | 0 | 0 | 0 |
| 8 | Epoxy/OH | 0 | 0 | 0 |

These examples demonstrate the following:

(1) It is important to include free radically active functional groups in the adhesives. Adhesives containing only cationically functional epoxy groups failed to exhibit measurable adhesion regardless of the type of composite. Similarly, regardless of the type of composite, it is desirable to limit the amount of cationically active functional groups in the adhesive, preferably such that the number of moles of cationically active functional groups per gram of resin is no greater than about 0.002.

(2) When bonding composites having cationically active functional groups, it is desirable to avoid the presence of cationically inhibiting groups such as urethane groups in quantities that can adversely affect cationic cure.

(3) Including functional groups such as hydroxyl groups in the adhesive composition that can covalently bond to components of the composite improves adhesion.

Examples 9–18 and Comparative Example 1

Eleven pre-adhesive compositions were prepared using M-101, BisGMA, HDDA, and UVR6105 as the basic ingredients, but varying the relative amounts of each ingredient. In each case, the initiator contained 0.25 parts CPQ, 0.25 parts EDMAB, and 0.50 parts CD1012. Each pre-adhesive composition was used to adhere a dental composite to a treated enamel surface, as described above, after which the shear adhesion was measured. The dental composite had the same composition as the Epoxy/Methacrylate Composite, described above. The results are shown in Table II.

TABLE II

| Example | M-101 | Bis-GMA | HDDA | UVR 6105 | moles epoxy/ g resin | Adhesion (MPA) |
|---|---|---|---|---|---|---|
| 9 | 0 | 50 | 50 | 0 | 0 | 14.3 |
| 10 | 20 | 50 | 30 | 0 | 0.0006 | 16.0 |
| 11 | 40 | 50 | 10 | 0 | 0.0013 | 17.0 |
| 12 | 50 | 50 | 0 | 0 | 0.0016 | 15.5 |
| 13 | 0 | 50 | 30 | 20 | 0.0016 | 17.2 |
| 14 | 0 | 50 | 10 | 40 | 0.0032 | 0.05 |
| 15 | 0 | 50 | 0 | 50 | 0.0040 | 0.05 |
| 16 | 60 | 40 | 0 | 0 | 0.0019 | 9.7 |
| 17 | 10 | 0 | 90 | 0 | 0.0003 | 4.6 |
| 18 | 60 | 0 | 40 | 0 | 0.0019 | 10.4 |
| Comp 1 | 100 | 0 | 0 | 0 | 0.0032 | 0.0 |

The results shown in Table II demonstrate the importance of including free radically active groups in the adhesive. For example, Comparative Example 1, which did not contain any free radically active groups, failed to display measurable adhesion. The results further demonstrate the importance of minimizing the amount of cationically active groups in the adhesive.

Other embodiments are within the following claims.

What is claimed is:

1. A method for treating hard tissue comprising:
   (a) applying to hard tissue a composition comprising a cationically active functional group, a free radically active functional group, and a polymerization initiator capable of initiating free radical polymerization, wherein the number of moles of said cationically active functional groups per gram of said composition is no greater than about 0.0075; and
   (b) exposing said composition to polymerization conditions to form an adhesive bonded to said hard tissue.

2. A method according to claim 1 wherein the number of moles of said cationically active functional groups per gram of said composition is no greater than about 0.002.

3. A method according to claim 1 further comprising treating said hard tissue prior to application of said composition with an agent selected from the group consisting of etchants, primers, adhesion promoters, and combinations thereof.

4. A method according to claim 1 comprising exposing said composition to visible light to form said adhesive bonded to said hard tissue.

5. A method according to claim 1 wherein said composition comprises an epoxy resin.

6. A method according to claim 1 wherein said composition comprises an ethylenically unsaturated compound.

7. A method according to claim 1 wherein said composition comprises an acrylic acid ester, a methacrylic acid ester, or a combination thereof.

8. A method according to claim 1 wherein said composition comprises a hydroxy-functional acrylic acid ester, a hydroxy-functional methacrylic acid ester, or a combination thereof.

9. A method according to claim 1 wherein said composition comprises (a) an epoxy resin and (b) an acrylic acid ester, a methacrylic acid ester, or a combination thereof.

10. A method according to claim 1 wherein said composition comprises a polymerizable component comprising a cationically active functional group and a free radically active functional group.

17

11. A method according to claim 10 wherein said polymerizable component comprises an epoxy-functional acrylic acid ester, methacrylic acid ester, or a combination thereof.

12. A method according to claim 1 wherein said initiator is capable of initiating free radical polymerization and cationic polymerization.

13. A method according to claim 1 wherein said initiator comprises an iodonium salt.

14. A method according to claim 1 wherein said initiator comprises an iodonium salt and a visible light sensitizer.

15. A method according to claim 1 wherein said initiator comprises an iodonium salt, a visible light sensitizer, and an electron donor,
wherein said initiator has a photoinduced potential greater than or equal to that of 3-dimethylamnino benzoic acid in a standard solution of $2.9 \times 10^{-5}$ moles/g diphenyl iodonium hexafluoroantimonate and $1.5 \times 10^{-5}$ moles/g camphorquinone in 2-butanone.

16. A method according to claim 1 wherein said composition comprises a hydroxy-functional component.

17. A method according to claim 16 wherein said hydroxy-functional component comprises a polyol.

18. A method according to claim 1 wherein the strength of the bond formed between said adhesive and said hard tissue is at least about 3 MPa.

19. A method according to claim 1 wherein said hard tissues comprises tooth enamel.

20. A method according to claim 1 wherein said hard tissue comprises dentin.

21. A method according to claim 1 further comprising applying a dental material to said adhesive.

22. A method according to claim 21 wherein said dental material comprises a dental composite.

23. A method according to claim 1 farther comprising applying a dental material to said composition prior to polymerization.

24. A method according to claim 23 wherein said dental material comprises a dental composite.

25. A method according to claim 22 or 24 wherein said dental composite comprises a cationically active functional group, a polymerization initiator, and a filler.

26. A method according to claim 25 wherein said dental composite further comprises a free radically active functional group.

27. A method according to claim 25 wherein said polymerization initiator of said dental composite is capable of initiating cationic polymerization.

28. A kit comprising:
(a) a composition comprising a cationically active functional group, a free radically active functional group, and a polymerization initiator capable of initiating free radical polymerization,
wherein the number of moles of said cationically active functional groups per gram of said composition is no greater than about 0.0075,
wherein said composition forms an adhesive capable of bonding to a tooth upon exposure to polymerization conditions; and
(b) a dental material capable of bonding to said adhesive.

29. A kit according to claim 28 wherein said dental material comprises a dental composite.

30. A kit according to claim 29 wherein said dental composite comprises a cationically active functional group, a polymerization initiator, and a filler.

31. A kit according to claim 30 wherein said dental composite further comprises a free radically active functional group.

18

32. A method for treating hard tissue comprising:
(a) applying to hard tissue a first polymerizable composition comprising a free radically active functional group and a polymerization initiator capable of initiating free radical polymerization,
said first composition being essentially free of polymerizable components having cationically active functional groups and being capable of forming an adhesive bonded to said hard tissue upon exposure to polymerization conditions;
(b) applying a second polymerizable composition comprising (i) a cationically active functional group and (ii) a polymerization initiator capable of initiating cationic polymerization; and
(c) exposing said second composition to polymerization conditions form a hardened composition adhered to said hard tissue.

33. A method according to claim 32 comprising exposing said first composition to polymerization conditions to form said adhesive prior to application of said second polymerizable composition.

34. A method according to claim 32 comprising exposing said first composition to polymerization conditions to form said adhesive subsequent to application of said second polymerizable composition.

35. A method according to claim 32 further comprising treating said hard tissue prior to application of said first composition with an agent selected from the group consisting of etchants, primers, adhesion promoters, and combinations thereof.

36. A method according to claim 32 wherein said first composition comprises a functional group capable of covalently bonding to said second composition.

37. A method according to claim 36 wherein said functional group comprises a hydroxyl group.

38. A method according to claim 32 wherein said first composition comprises a polyol.

39. A method according to claim 32 wherein said first composition comprises a component having a free radically active functional group and a functional group capable of covalently bonding to said second composition.

40. A method according to claim 32 wherein said first composition comprises a hydroxy-fuictional acrylic acid ester, a hydroxy-functional methacrylic acid ester, or a combination thereof.

41. A method according to claim 32 wherein said second composition comprises an epoxy resin.

42. A method according to claim 32 wherein said second composition further comprises a free radically active functional group.

43. A method according to claim 42 wherein said second composition comprises an acrylic acid ester, a methacrylic acid ester, or a combination thereof.

44. A method according to claim 32 wherein said second composition comprises a component comprising a cationically active functional group and a free radically active functional group.

45. A method according to claim 32 wherein at least one of said initiators comprises an iodonium salt.

46. A method according to claim 32 wherein at least one of said initiators comprises an iodonium salt and a visible light sensitizer.

47. A method according to claim 32 wherein at least one of said initiators comprises an iodonium salt, a visible light sensitizer, and an electron donor,
wherein said initiator has a photoinduced potential greater than or equal to that of 3-dimethylamino benzoic acid in a standard solution of $2.9 \times 10^{-5}$ moles/g diphenyl iodonium hexafluoroantimonate and $1.5 \times 10^{-5}$ moles/g camphorquinone in 2-butanone.

48. A method according to claim 32 wherein said hard tissue comprises tooth enamel.

49. A method according to claim 32 wherein said hard tissue comprises dentin.

50. A method according to claim 32 wherein said second composition comprises a dental material.

51. A method according to claim 32 wherein said second composition comprises a dental composite.

52. A kit comprising:
   (a) a first polymerizable composition comprising a free radically active functional group and a polymerization initiator capable of initiating free radical polymerization,
   said first composition being essentially free of polymerizable components having cationically active functional groups,
   wherein said first composition forms an adhesive capable of bonding to a tooth upon exposure to polymerization conditions; and
   (b) a second polymerizable composition comprising a cationically active functional group and a polymerization initiator capable of initiating cationic polymerization,
   wherein said second composition forms a hardened composition adhered to the tooth upon exposure to polymerization conditions.

53. A kit according to claim 52 wherein said first composition comprises a hydroxy-functional component capable of covalently bonding to said second composition.

54. A kit according to claim 52 wherein said second composition comprises a dental composition.

* * * * *

UNITED STATES PATENT AND TRADEMARK OFFICE
CERTIFICATE OF CORRECTION

PATENT NO.: 5,980,253

DATED: November 9, 1999

INVENTOR(S): Joel D. Oxman, Hoa T. Bui and Dwight W. Jacobs

It is certified that error appears in the above-identified patent and that said Letters Patent is hereby corrected as shown below:

Col. 17, line 33 (claim 23), replace "farther" with --further--.

Col. 18, line 43 (claim 40), replace "hydroxy-fuictional" with --hydroxy-functional--.

Signed and Sealed this

Nineteenth Day of December, 2000

Q. TODD DICKINSON

Attest:

Attesting Officer

Commissioner of Patents and Trademarks